US010434267B2

(12) United States Patent
Akouka et al.

(10) Patent No.: US 10,434,267 B2
(45) Date of Patent: *Oct. 8, 2019

(54) INHALATION DEVICE AND METHOD

(71) Applicant: MICRODOSE THERAPEUTX, INC., Monmouth Junction, NJ (US)

(72) Inventors: Henri M. Akouka, Mount Laurel, NJ (US); Daniel P. Becker, Washington Crossing, PA (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 773 days.

This patent is subject to a terminal disclaimer.

(21) Appl. No.: 15/098,035

(22) Filed: Apr. 13, 2016

(65) Prior Publication Data

US 2016/0220771 A1    Aug. 4, 2016

Related U.S. Application Data

(60) Continuation of application No. 14/056,828, filed on Oct. 17, 2013, now Pat. No. 9,974,909, which is a
(Continued)

(51) Int. Cl.
*A61M 15/00* (2006.01)
*A61M 16/00* (2006.01)

(52) U.S. Cl.
CPC ...... *A61M 15/0051* (2014.02); *A61M 15/001* (2014.02); *A61M 15/005* (2014.02);
(Continued)

(58) Field of Classification Search
CPC .......... A61M 15/0051; A61M 15/0041; A61M 15/0045; A61M 15/0065; A61M 15/0085;
(Continued)

(56) References Cited

U.S. PATENT DOCUMENTS

| 1,419,619 A | 6/1922 | Deming .................... 424/438 |
| 1,580,576 A | 4/1926 | Weidner .................... 510/146 |

(Continued)

FOREIGN PATENT DOCUMENTS

| CA | 2 451 519 | 9/2003 | ............. A61K 9/20 |
| DE | 102005005540 | 8/2006 | ............ A61M 15/00 |

(Continued)

OTHER PUBLICATIONS

European Search Report issued in application No. 18193682.4, dated Nov. 13, 2018 (7 pgs).
(Continued)

*Primary Examiner* — Colin W Stuart
*Assistant Examiner* — Douglas Y Sul
(74) *Attorney, Agent, or Firm* — Hayes Soloway P.C.

(57) ABSTRACT

The present disclosure provides a method and device for delivering a pharmaceutical to the airway of a human or animal patient. In one aspect, the device includes a dose drum formed into a cylinder and including a plurality of dose compartments for containing individual doses. In another aspect, the device may include a reservoir containing a pharmaceutical material in bulk form and a metering recess for metering the pharmaceutical material to form a pharmaceutical dose. Another aspect provides an inhaler with a combined reservoir and dosing chamber configured to contain multiple doses of a pharmaceutical material.

5 Claims, 10 Drawing Sheets

Related U.S. Application Data division of application No. 12/985,158, filed on Jan. 5, 2011, now Pat. No. 8,991,390.

(60) Provisional application No. 61/292,404, filed on Jan. 5, 2010, provisional application No. 61/292,403, filed on Jan. 5, 2010, provisional application No. 61/292,401, filed on Jan. 5, 2010.

(52) U.S. Cl.
CPC .... *A61M 15/0021* (2014.02); *A61M 15/0043* (2014.02); *A61M 15/0045* (2013.01); *A61M 15/0055* (2014.02); *A61M 15/0065* (2013.01); *A61M 15/0085* (2013.01); *A61M 2016/0021* (2013.01); *A61M 2202/0266* (2013.01); *A61M 2202/062* (2013.01); *A61M 2202/064* (2013.01); *A61M 2205/0294* (2013.01); *A61M 2205/12* (2013.01); *A61M 2205/8206* (2013.01); *A61M 2250/00* (2013.01)

(58) Field of Classification Search
CPC ............ A61M 15/0043; A61M 15/005; A61M 15/0055; A61M 15/001; A61M 15/0021; A61M 15/0038; A61M 15/004; A61M 15/0028; A61M 15/0035; A61M 11/007; A61M 2205/0205; A61M 2205/12

See application file for complete search history.

(56) References Cited

U.S. PATENT DOCUMENTS

| | | | |
|---|---|---|---|
| 2,102,885 A | 12/1937 | Carroll | 206/530 |
| 2,340,037 A | 1/1944 | Zipper | 424/453 |
| 2,517,482 A | 8/1950 | Hall | 128/206 |
| 3,048,526 A | 8/1962 | Boswell | 424/472 |
| 3,241,625 A | 3/1966 | Soojan | 177/120 |
| 3,367,535 A | 2/1968 | Tanguay | 221/71 |
| 3,410,450 A | 11/1968 | Fortenberry | 221/7 |
| 3,437,074 A | 4/1969 | Hagopian et al. | 118/623 |
| 3,507,277 A | 4/1970 | Altounyan et al. | 128/807 |
| 3,518,992 A | 7/1970 | Altounyan et al. | 128/807 |
| 3,620,759 A | 11/1971 | Maddox | 426/78 |
| 3,635,219 A | 1/1972 | Altounyan et al. | 128/266 |
| 3,653,380 A | 4/1972 | Hansen | 128/203.15 |
| 3,702,653 A | 11/1972 | Motten | 206/534 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| D235,215 S | 5/1975 | Larson | D24/104 |
| 3,889,636 A | 6/1975 | Smith | 118/621 |
| 3,943,437 A | 3/1976 | Mourier | 324/32 |
| 3,948,264 A | 4/1976 | Wilke et al. | 128/203.15 |
| 3,977,323 A | 8/1976 | Pressman et al. | 101/426 |
| 3,999,119 A | 12/1976 | Bares | 324/32 |
| 4,021,587 A | 5/1977 | Banker | 427/18 |
| 4,069,084 A | 1/1978 | Mlodozeniec et al. | 156/378 |
| 4,071,169 A | 1/1978 | Dunn | 222/76 |
| 4,072,249 A | 2/1978 | Ekenstam et al. | 222/95 |
| 4,094,317 A | 6/1978 | Wasnich | 128/200.16 |
| 4,170,289 A | 10/1979 | McDonald et al. | 424/21 |
| 4,182,447 A | 1/1980 | Kay | 206/220 |
| 4,196,564 A | 4/1980 | Bodenmann et al. | 53/471 |
| 4,196,565 A | 4/1980 | Bodenmann et al. | 53/471 |
| 4,197,289 A | 4/1980 | Sturzenegger et al. | 424/21 |
| 4,204,766 A | 5/1980 | Harada | 356/404 |
| 4,240,418 A | 12/1980 | Rosskamp et al. | 128/203.15 |
| D258,091 S | 1/1981 | Reed et al. | D24/101 |
| 4,247,006 A | 1/1981 | Bodenmann et al. | 206/528 |
| 4,250,997 A | 2/1981 | Bodenmann et al. | 206/528 |
| 4,252,434 A | 2/1981 | Nakamura et al. | 355/15 |
| 4,255,777 A | 3/1981 | Kelly | 361/228 |
| 4,339,428 A | 7/1982 | Tencza | 424/21 |
| 4,349,531 A | 9/1982 | Mlodozeniec et al. | 424/27 |
| 4,376,111 A | 3/1983 | Tovey | 424/467 |
| 4,379,969 A | 4/1983 | Cobb et al. | 250/324 |
| D269,718 S | 7/1983 | Tovey | D24/101 |
| D269,721 S | 7/1983 | Tovey | D24/101 |
| D269,722 S | 7/1983 | Tovey | D24/101 |
| 4,399,699 A | 8/1983 | Fujishiro | 73/304 |
| 4,452,239 A | 6/1984 | Malem | 128/200.17 |
| D274,846 S | 7/1984 | Eoga | D24/101 |
| 4,514,781 A | 4/1985 | Plasschaert et al. | 361/230 |
| 4,555,174 A | 11/1985 | Kramer | 355/3 DD |
| D283,649 S | 4/1986 | Casberg | D23/207 |
| 4,594,901 A | 6/1986 | Norman | 73/861.04 |
| 4,601,896 A | 7/1986 | Nugent | 424/453 |
| D285,363 S | 8/1986 | Tovey | D24/101 |
| D286,085 S | 10/1986 | Tovey | D24/101 |
| 4,626,876 A | 12/1986 | Miyagawa et al. | 346/160 |
| 4,627,432 A | 12/1986 | Newell et al. | 128/203.15 |
| 4,643,731 A | 2/1987 | Eckenhoff | 604/892.1 |
| 4,721,060 A | 1/1988 | Cannon et al. | 119/15 |
| 4,733,797 A | 3/1988 | Haber | 221/8 |
| 4,734,722 A | 3/1988 | Maczuszenko et al. | 346/159 |
| 4,735,805 A | 4/1988 | Ni et al. | 424/464 |
| 4,772,470 A | 9/1988 | Inoue et al. | 424/435 |
| 4,790,305 A | 12/1988 | Zoltan et al. | 128/200.23 |
| 4,795,644 A | 1/1989 | Zentner | 424/468 |
| 4,848,267 A | 7/1989 | Slayton et al. | 118/653 |
| 4,875,060 A | 10/1989 | Masuda et al. | 346/155 |
| 4,878,454 A | 11/1989 | Cann | 118/663 |
| 4,883,182 A | 11/1989 | Hughes | 206/534 |
| 5,005,516 A | 4/1991 | Speer | 118/657 |
| 5,009,894 A | 4/1991 | Hsiao | 424/451 |
| 5,055,306 A | 10/1991 | Barry et al. | 424/482 |
| 5,074,426 A | 12/1991 | Goodhart et al. | 220/4.24 |
| 5,075,114 A | 12/1991 | Roche | 424/470 |
| 5,102,045 A | 4/1992 | Diana | 239/3 |
| 5,129,572 A | 7/1992 | Keilberth et al. | 228/131 |
| 5,152,284 A | 10/1992 | Valentini et al. | 128/203.21 |
| 5,192,528 A | 3/1993 | Radhakrishnan et al. | 424/45 |
| 5,204,055 A | 4/1993 | Sachs et al. | 419/2 |
| 5,207,217 A | 5/1993 | Cocozza et al. | 128/203.21 |
| 5,207,705 A | 5/1993 | Trudell et al. | 623/1 |
| 5,214,386 A | 5/1993 | Singer et al. | 324/452 |
| 5,260,321 A | 11/1993 | Hof et al. | 514/338 |
| 5,284,133 A | 2/1994 | Burns et al. | 128/200.23 |
| 5,297,502 A | 3/1994 | Jaeger | 119/15 |
| 5,344,043 A | 9/1994 | Moulding et al. | 221/71 |
| 5,349,947 A | 9/1994 | Newhouse et al. | 128/203.21 |
| 5,404,871 A | 4/1995 | Goodman et al. | 128/200.14 |
| 5,415,162 A | 5/1995 | Casper | 128/203.12 |
| 5,417,980 A | 5/1995 | Goldman et al. | 424/464 |
| 5,421,816 A | 6/1995 | Lipkovker | 604/20 |
| 5,429,302 A | 7/1995 | Abbott | 239/102.2 |
| 5,454,271 A | 10/1995 | Yamamoto et al. | 73/861.04 |
| 5,458,135 A | 10/1995 | Patton et al. | 128/200.14 |
| 5,487,378 A | 1/1996 | Robertson et al. | 128/200.16 |
| 5,487,901 A | 1/1996 | Conte et al. | 424/472 |
| 5,490,962 A | 2/1996 | Cima et al. | 264/22 |
| 5,492,112 A | 2/1996 | Mecikalski et al. | 128/203.15 |
| 5,497,763 A | 3/1996 | Lloyd et al. | 128/200.14 |
| 5,508,040 A | 4/1996 | Chen | 424/451 |
| 5,544,646 A | 8/1996 | Lloyd et al. | 128/200.14 |
| 5,575,280 A | 11/1996 | Gupta et al. | 128/203.15 |
| D376,643 S | 12/1996 | Hatton et al. | D24/101 |
| 5,590,645 A | 1/1997 | Davies | 128/203.15 |
| 5,629,316 A | 5/1997 | Kurihara et al. | 514/263.32 |
| 5,655,523 A | 8/1997 | Hodson et al. | 128/315 |
| 5,669,973 A | 9/1997 | Pletcher | 118/624 |
| 5,672,359 A | 9/1997 | Digenis et al. | 424/463 |
| 5,672,581 A | 9/1997 | Rubsamen et al. | 514/3 |
| 5,694,920 A | 12/1997 | Abrams et al. | 128/200.16 |
| 5,699,649 A | 12/1997 | Abrams et al. | 53/428 |
| 5,714,007 A | 2/1998 | Pletcher et al. | 118/629 |
| 5,724,959 A | 3/1998 | McAughey et al. | 128/203.15 |
| 5,727,546 A | 3/1998 | Clarke et al. | 128/203.15 |
| 5,740,793 A | 4/1998 | Hodson et al. | 128/203.15 |
| 5,758,823 A | 6/1998 | Glezer et al. | 239/4 |
| 5,794,612 A | 8/1998 | Wachter et al. | 128/200.23 |
| 5,805,768 A | 9/1998 | Schwartz et al. | 392/390 |
| 5,823,183 A | 10/1998 | Casper et al. | 128/203.15 |

(56) References Cited

U.S. PATENT DOCUMENTS

| | | | |
|---|---|---|---|
| 5,823,434 A | 10/1998 | Cooper | 239/102.2 |
| 5,827,538 A | 10/1998 | Cussler et al. | 424/473 |
| 5,849,706 A | 12/1998 | Molina y Vedia et al. | 514/12 |
| 5,853,002 A | 12/1998 | Kawasaki | 128/200.14 |
| 5,858,099 A | 1/1999 | Sun et al. | 118/621 |
| 5,873,360 A | 2/1999 | Davies et al. | 128/203.15 |
| 5,881,719 A | 3/1999 | Gottenauer et al. | 128/203.15 |
| 5,884,624 A | 3/1999 | Barnett et al. | 128/206.24 |
| 5,894,990 A | 4/1999 | Glezer et al. | 239/423 |
| 5,906,202 A | 5/1999 | Schuster et al. | 128/203.23 |
| 5,908,158 A | 6/1999 | Cheiman | 239/102.2 |
| 5,921,237 A | 7/1999 | Eisele et al. | 128/203.21 |
| 5,938,118 A | 8/1999 | Cooper | 239/102.2 |
| 5,944,012 A | 8/1999 | Pera | 128/203.15 |
| 5,954,049 A | 9/1999 | Foley et al. | 128/203.29 |
| 5,960,609 A | 10/1999 | Abrams et al. | 53/428 |
| 6,009,690 A | 1/2000 | Rosenberg et al. | 53/454 |
| 6,012,454 A | 1/2000 | Hodson et al. | 128/203.15 |
| 6,013,280 A | 1/2000 | Frisbee et al. | 424/464 |
| D420,464 S | 2/2000 | Binstock et al. | D28/8.1 |
| 6,026,809 A | 2/2000 | Abrams et al. | 128/203.15 |
| 6,027,748 A | 2/2000 | Conte et al. | 424/458 |
| 6,029,663 A | 2/2000 | Eisele et al. | 128/203.21 |
| D421,800 S | 3/2000 | Doat | D24/110 |
| 6,032,666 A | 3/2000 | Davies et al. | 128/203.15 |
| 6,032,871 A | 3/2000 | Borner et al. | 239/3 |
| 6,074,688 A | 6/2000 | Pletcher et al. | 427/2.14 |
| 6,092,522 A | 7/2000 | Calvert et al. | 128/203.21 |
| 6,136,344 A | 10/2000 | Depui et al. | 424/470 |
| 6,142,146 A | 11/2000 | Abrams et al. | 128/203.15 |
| 6,152,130 A | 11/2000 | Abrams et al. | 128/204.21 |
| 6,153,218 A | 11/2000 | Barnwell et al. | 424/451 |
| 6,187,291 B1 | 2/2001 | Weinstein et al. | 424/45 |
| 6,197,331 B1 | 3/2001 | Lerner et al. | 424/448 |
| 6,209,538 B1 | 4/2001 | Casper et al. | 128/203.15 |
| 6,226,962 B1 | 5/2001 | Eason et al. | 128/203.15 |
| 6,240,917 B1 | 6/2001 | Andrade | 128/200.23 |
| 6,294,582 B1 | 9/2001 | Jerussi | 514/617 |
| 6,312,909 B1 | 11/2001 | Shyjan | 435/6 |
| 6,319,541 B1 | 11/2001 | Pletcher et al. | 427/2.14 |
| 6,328,033 B1 | 12/2001 | Avrahami | 128/203.15 |
| 6,347,629 B1 | 2/2002 | Braithwaite | 128/203.15 |
| 6,350,468 B1 | 2/2002 | Sanso | 424/456 |
| 6,367,470 B1 | 4/2002 | Denyer et al. | 128/200.14 |
| 6,415,790 B1 | 7/2002 | Leedom et al. | 128/203.15 |
| 6,428,809 B1 | 8/2002 | Abrams et al. | 424/451 |
| 6,457,654 B1 | 10/2002 | Glezer et al. | 239/4 |
| 6,526,966 B1 | 3/2003 | Peesay | 128/200.21 |
| 6,536,427 B2 | 3/2003 | Davies et al. | 128/203.15 |
| 6,536,432 B2 | 3/2003 | Truschel | 128/205.23 |
| 6,543,442 B2 | 4/2003 | Gonda et al. | 128/200.14 |
| 6,543,443 B1 | 4/2003 | Klimowicz et al. | 128/200.23 |
| 6,616,914 B2 | 9/2003 | Ward et al. | 424/45 |
| 6,622,720 B2 | 9/2003 | Hadimioglu | 128/200.16 |
| 6,622,723 B1 | 9/2003 | Nilsson | 128/203.12 |
| 6,626,173 B2 | 9/2003 | Genova et al. | 128/203.15 |
| 6,629,646 B1 | 10/2003 | Ivri | 239/4 |
| 6,684,879 B1 | 2/2004 | Coffee et al. | 128/200.14 |
| 6,698,425 B1 | 3/2004 | Widerstrom | 128/203.25 |
| 6,702,683 B2 | 3/2004 | Abrams et al. | 464/465 |
| 6,722,581 B2 | 4/2004 | Saddoughi | 239/102.2 |
| 6,737,044 B1 | 5/2004 | Dickinson et al. | 424/46 |
| 6,748,944 B1 | 6/2004 | Della Vecchia | 128/200.16 |
| 6,759,159 B1 | 7/2004 | Gray et al. | 429/71 |
| 6,779,520 B2 | 8/2004 | Genova et al. | 128/200.22 |
| 6,792,945 B2 | 9/2004 | Davies et al. | 128/203.15 |
| 6,840,239 B2 | 1/2005 | Myrman | 128/203.15 |
| 6,869,615 B2 | 3/2005 | Chen et al. | 424/469 |
| 6,871,647 B2 | 3/2005 | Allan et al. | 128/203.21 |
| 6,889,690 B2 | 5/2005 | Crowder et al. | 128/203.15 |
| 6,901,929 B2 | 6/2005 | Burr et al. | 128/203.15 |
| 6,904,912 B2 | 6/2005 | Roy et al. | 128/203.18 |
| 6,962,266 B2 | 11/2005 | Morgan et al. | 221/25 |
| 6,971,383 B2 | 12/2005 | Hickey et al. | 128/203.15 |
| 7,025,056 B2 | 4/2006 | Eason | 128/203.15 |
| D520,635 S | 5/2006 | Bonny et al. | D24/104 |
| 7,077,126 B2 | 7/2006 | Kummer et al. | 128/200.23 |
| 7,080,644 B2 | 7/2006 | Gumaste | 128/203.15 |
| D530,814 S | 10/2006 | Bonny et al. | D24/104 |
| 7,117,867 B2 | 10/2006 | Cox | 128/200.14 |
| 7,118,010 B2 | 10/2006 | Crowder et al. | 221/1 |
| D535,741 S | 1/2007 | Stawski et al. | D24/101 |
| 7,231,920 B2 | 6/2007 | Harvey et al. | 128/203.15 |
| 7,233,228 B2 | 6/2007 | Lintell | 340/309.7 |
| 7,290,541 B2 | 11/2007 | Ivri et al. | 128/200.14 |
| D556,946 S | 12/2007 | Seum | D28/8.1 |
| 7,318,434 B2 | 1/2008 | Gumaste et al. | 128/203.15 |
| 7,334,577 B2 | 2/2008 | Gumaste et al. | 128/203.15 |
| D564,086 S | 3/2008 | Nielsen et al. | D24/101 |
| 7,343,914 B2 | 3/2008 | Abrams et al. | 128/200.23 |
| 7,451,764 B2 | 11/2008 | Wang | 128/206.18 |
| 7,527,021 B2 | 5/2009 | Mead et al. | 119/420 |
| 7,538,473 B2 | 5/2009 | Blandino et al. | 310/317 |
| 7,607,435 B2 | 10/2009 | Lipp | 128/203.13 |
| 7,748,382 B2 | 7/2010 | Denyer et al. | 128/204.21 |
| 7,779,837 B2 | 8/2010 | Gumaste et al. | 128/203.15 |
| 7,810,495 B2 | 10/2010 | Gumaste | 128/203.23 |
| 7,950,390 B2 | 5/2011 | Gumaste | 128/203.21 |
| 8,196,576 B2 | 6/2012 | Kriksunov et al. | 128/203.15 |
| 8,322,338 B2 | 12/2012 | Gumaste et al. | 128/203.15 |
| 8,371,294 B2 | 2/2013 | Gumaste et al. | 128/200.24 |
| 8,439,033 B2 | 5/2013 | Gumaste et al. | 128/204.21 |
| 8,511,304 B2 | 8/2013 | Anderson et al. | 128/203.25 |
| 8,991,390 B2 | 3/2015 | Akouka et al. | A61M 15/00 |
| 9,132,246 B2 | 9/2015 | Gumaste et al. | 128/203.25 |
| 2001/0006656 A1 | 7/2001 | Harlan et al. | 424/400 |
| 2002/0013334 A1 | 1/2002 | Robl et al. | 514/291 |
| 2002/0032409 A1 | 3/2002 | Ritsche | 604/154 |
| 2002/0053344 A1 | 5/2002 | Davies et al. | 128/203.15 |
| 2002/0078947 A1 | 6/2002 | Gumaste | 128/200.14 |
| 2002/0103443 A1 | 8/2002 | Roy et al. | 600/532 |
| 2002/0129812 A1 | 9/2002 | Litherland et al. | 128/200.14 |
| 2003/0041859 A1 | 3/2003 | Abrams et al. | 128/200.22 |
| 2003/0075172 A1 | 4/2003 | Johnson et al. | 128/200.24 |
| 2003/0192539 A1 | 10/2003 | Myrman | 128/203.15 |
| 2003/0192540 A1 | 10/2003 | Myrman et al. | 128/203.15 |
| 2004/0033256 A1 | 2/2004 | Margalit | 424/450 |
| 2004/0089298 A1 | 5/2004 | Haikarainen et al. | 128/203.15 |
| 2004/0142036 A1 | 7/2004 | Abrams et al. | 424/473 |
| 2004/0156903 A1 | 8/2004 | Abrams et al. | 424/473 |
| 2004/0185100 A1 | 9/2004 | Franz | 424/472 |
| 2004/0224020 A1 | 11/2004 | Schoenhard | 424/471 |
| 2004/0250812 A1 | 12/2004 | Davies et al. | 128/200.14 |
| 2004/0263567 A1 | 12/2004 | Hess et al. | 347/47 |
| 2005/0008690 A1 | 1/2005 | Miller | 424/451 |
| 2005/0026909 A1 | 2/2005 | Landau et al. | 514/218 |
| 2005/0053649 A1 | 3/2005 | Chalmers | 424/451 |
| 2005/0087189 A1 | 4/2005 | Crockford et al. | 128/203.15 |
| 2005/0109659 A1 | 5/2005 | Hickey et al. | 206/538 |
| 2005/0121027 A1 | 6/2005 | Nilsson et al. | 128/200.23 |
| 2005/0154491 A1 | 7/2005 | Anderson et al. | 700/236 |
| 2005/0155601 A1 | 7/2005 | Steiner et al. | 128/200.23 |
| 2005/0172962 A1 | 8/2005 | Gumaste et al. | 128/203.21 |
| 2005/0174216 A1 | 8/2005 | Lintell | 340/309.16 |
| 2005/0183724 A1 | 8/2005 | Gumaste et al. | 128/203.15 |
| 2005/0183725 A1 | 8/2005 | Gumaste et al. | 128/203.15 |
| 2005/0267628 A1 | 12/2005 | Crowder et al. | 700/240 |
| 2006/0147389 A1 | 7/2006 | Staniforth | 424/46 |
| 2006/0157053 A1 | 7/2006 | Barney | 128/200.23 |
| 2006/0163269 A1 | 7/2006 | Anderson et al. | 221/72 |
| 2006/0174869 A1 | 8/2006 | Gumaste et al. | 128/200.14 |
| 2006/0191534 A1 | 8/2006 | Hickey et al. | 128/200.14 |
| 2006/0213503 A1 | 9/2006 | Borgschulte et al. | 128/200.14 |
| 2006/0257327 A1 | 11/2006 | Zierenberg et al. | 424/46 |
| 2007/0059248 A1 | 3/2007 | Unger et al. | 424/9.52 |
| 2007/0060652 A1 | 3/2007 | Fraser et al. | 514/561 |
| 2007/0087048 A1 | 4/2007 | Abrams et al. | 424/451 |
| 2007/0119969 A1 | 5/2007 | Collins et al. | 239/102.1 |
| 2007/0137645 A1 | 6/2007 | Eason et al. | 128/203.15 |
| 2007/0215152 A1 | 9/2007 | Goede et al. | 128/203.15 |
| 2007/0221218 A1 | 9/2007 | Warden et al. | 128/203.15 |
| 2007/0240712 A1 | 10/2007 | Fleming et al. | 128/203.15 |
| 2008/0115784 A1 | 5/2008 | Gumaste et al. | 128/203.15 |
| 2008/0202514 A1 | 8/2008 | Kriksunov et al. | 128/203.15 |

(56) References Cited

U.S. PATENT DOCUMENTS

| | | | |
|---|---|---|---|
| 2008/0295834 A1 | 12/2008 | Thoemmes et al. | 128/203.21 |
| 2009/0000615 A1 | 1/2009 | Pohlmann et al. | 128/200.21 |
| 2009/0007908 A1 | 1/2009 | Eason et al. | 128/203.15 |
| 2009/0020113 A1 | 1/2009 | Watanabe | 128/200.14 |
| 2009/0095294 A1 | 4/2009 | Smyth et al. | 128/203.15 |
| 2009/0308390 A1 | 12/2009 | Smutney et al. | 128/203.15 |
| 2010/0139654 A1 | 6/2010 | Thoemmes et al. | 128/203.15 |
| 2010/0252032 A1 | 10/2010 | Thoemmes et al. | 128/200.23 |
| 2010/0294278 A1 | 11/2010 | Mosier et al. | 128/203.14 |
| 2011/0000481 A1 | 1/2011 | Gumaste et al. | 128/200.23 |
| 2011/0041844 A1 | 2/2011 | Dunne | 128/203.12 |
| 2013/0255678 A1 | 10/2013 | Gumaste et al. | 128/203.15 |
| 2015/0231347 A1 | 8/2015 | Gumaste et al. | A61M 15/0085 |

FOREIGN PATENT DOCUMENTS

| | | | |
|---|---|---|---|
| DE | 102009005048 | 7/2010 | A61H 31/02 |
| EP | 0 308 637 | 3/1989 | A61K 9/48 |
| EP | 0431924 | 1/1996 | B29C 67/24 |
| EP | 0885662 | 12/1998 | B05D 1/06 |
| EP | 0891817 | 1/1999 | B05B 5/08 |
| EP | 1 166 812 | 1/2002 | A61M 15/00 |
| EP | 1 499 276 | 1/2005 | A61J 7/00 |
| EP | 1 534 366 | 1/2005 | A61M 15/00 |
| EP | 0 799 076 | 3/2005 | A62B 18/00 |
| EP | 1 124 602 | 4/2005 | A61M 11/06 |
| EP | 1 522 325 | 4/2005 | A61M 15/00 |
| EP | 1 617 820 | 1/2006 | A61K 47/18 |
| EP | 1 691 781 | 8/2006 | A61J 1/00 |
| EP | 1 713 530 | 10/2006 | A61B 5/08 |
| EP | 1 986 721 | 11/2008 | A61M 15/00 |
| EP | 1 581 291 | 1/2009 | A61M 15/00 |
| EP | 2 054 167 | 5/2009 | B06B 1/02 |
| EP | 1 292 347 | 10/2009 | A61M 15/00 |
| EP | 1 691 783 | 11/2009 | A61K 9/14 |
| EP | 2 162 174 | 3/2010 | A61M 15/00 |
| EP | 2 016 965 | 5/2010 | A61M 11/00 |
| EP | 2 047 881 | 8/2010 | A61M 15/00 |
| EP | 2 234 728 | 10/2010 | A61M 15/00 |
| EP | 1 706 099 | 5/2011 | A61K 9/14 |
| GB | 2264237 | 8/1993 | A61M 15/00 |
| JP | 4277126 | 10/1992 | 198/690.1 |
| JP | H06502784 | 3/1994 | A61M 13/00 |
| JP | 9-501413 | 2/1997 | A61K 38/00 |
| JP | 2000503866 | 4/2000 | A61M 15/00 |
| JP | 2002-047177 | 2/2002 | A61K 31/192 |
| JP | 2003526480 | 9/2003 | A61M 13/00 |
| JP | 2003533294 | 11/2003 | A61M 15/00 |
| JP | 2004512146 | 4/2004 | A61M 13/00 |
| JP | 2005515039 | 5/2005 | A61J 7/02 |
| JP | 2009532189 | 9/2009 | A61M 15/00 |
| RU | 2286784 | 11/2006 | A61K 9/20 |
| WO | WO9209322 | 6/1992 | A61M 15/00 |
| WO | WO 94/28726 | 12/1994 | A61K 37/02 |
| WO | WO 95/16438 | 6/1995 | A61K 37/02 |
| WO | WO 96/13294 | 5/1996 | A61M 15/00 |
| WO | WO 97/26934 | 7/1997 | A61M 15/00 |
| WO | WO 9725065 | 7/1997 | A61K 45/06 |
| WO | WO 980033 | 1/1998 | B65B 1/30 |
| WO | WO 98/32479 | 7/1998 | A61M 15/00 |
| WO | WO 98/36770 | 8/1998 | A61K 38/27 |
| WO | WO 98/42446 | 10/1998 | B05B 5/025 |
| WO | WO 99/30693 | 6/1999 | A61K 9/48 |
| WO | WO 99/64095 | 12/1999 | A61J 3/00 |
| WO | WO 99/65550 | 12/1999 | A61M 15/00 |
| WO | WO 00/71108 | 11/2000 | A61K 31/00 |
| WO | WO 01/32127 | 5/2001 | A61K 45/00 |
| WO | WO 01/52815 | 7/2001 | A61K 9/00 |
| WO | WO 01/64182 | 9/2001 | A61K 45/00 |
| WO | WO0168169 | 9/2001 | A61M 15/00 |
| WO | WO0172605 | 10/2001 | B65D 83/04 |
| WO | WO 02/04055 | 1/2002 | A61M 11/00 |
| WO | WO0236188 | 5/2002 | A61M 15/00 |
| WO | WO 02/096347 | 12/2002 | |
| WO | WO 03/039464 | 5/2003 | A61K 31/00 |
| WO | WO 03039464 | 5/2003 | A61K 31/00 |
| WO | WO 03/092576 | 11/2003 | A61J 7/04 |
| WO | WO 2004/002394 | 1/2004 | |
| WO | WO 2004/039763 | 5/2004 | C07C 219/20 |
| WO | WO 2004/093848 | 11/2004 | A61K 9/16 |
| WO | WO2005041848 | 5/2005 | A61J 1/03 |
| WO | WO 2005/053646 | 6/2005 | A61K 9/14 |
| WO | WO 2005/074455 | 8/2005 | |
| WO | WO 2006/047427 | 5/2006 | A61K 31/216 |
| WO | WO 2007/096111 | 8/2007 | A61M 15/00 |
| WO | WO2007121097 | 10/2007 | A61M 15/00 |
| WO | WO 2008/021281 | 2/2008 | |
| WO | WO 2009/007068 | 1/2009 | A61M 15/00 |
| WO | WO 2009/090084 | 7/2009 | A61M 15/00 |
| WO | WO 2011/160932 | 12/2011 | A61M 15/00 |
| WO | WO 2011/163272 | 12/2011 | A61M 15/00 |

OTHER PUBLICATIONS

Japanese Patent Decision (w/transcript) issued in application No. 2016-096893, dated Dec. 20, 2018 (4 pgs).
Japanese Office Action issued in application No. 2016-096893, dated Nov. 15, 2017 (12 pgs).
Japanese Decision to Grant a Patent issued in appln. No. 2015-246356, dated Dec. 15, 2017, and English machine translation (7 pgs).
Notice of Allowance issued in U.S. Appl. No. 14/056,828 dated Jan. 18, 2018 (21 pgs).
Canadian Office Action issued in application No. 2,784,041, dated Nov. 4, 2016 (4 pgs).
Chinese Office Action issued in application No. 201410539433.4, dated Jan. 4, 2017 (10 pgs).
Japanese Office Action issued in application No. 2015-246356 (with translation), dated Oct. 31, 2016 (10 pgs).
Office Action issued in U.S. Appl. No. 14/056,828, dated Nov. 14, 2016 (33 pages).
Taiwan Office Action issued in application No. 100100398 (with translation), dated Oct. 31, 2016 (6 pgs).
Japanese Office Action issued in application No. 2014-210159, dated May 27, 2016 (4 pgs).
Chinese Office Action issued in application No. 201410539433.4, dated May 5, 2016 (12 pgs).
European Intention to Grant issued in application No. 11 732 098.6, dated May 29, 2018 (7 pgs).
Japanese Office Action (w/translation) issued in application No. 2016-096893, dated Jun. 19, 2018 (8 pgs).
Office Action issued in U.S. Appl. No. 14/056,828, dated Jun. 20, 2017 (37 pgs).
U.S. Appl. No. 60/727,029, filed Oct. 14, 2005, Microdose Technologies, Inc.
"Guidance for Industry-Nonclinical Safety Evaluation of Drug Combinations", U.S. Department of Health and Human Services, Food and Drug Administration, Center for Drug Evaluation and Research (CDER), Pharmacology and Toxicology, Jan. 2005.
"Nebulizer", http://en.wikipedia.org/wiki/Nebulizer, Jun. 26, 2009, 2 pgs.
Canadian Office Action issued in application 2,784,041, dated Feb. 27, 2015 (3 pgs).
Canadian Office Action issued in application No. 2,784,041, dated Dec. 8, 2015 (3 pgs).
Chilean Official Action + Translation dated Mar. 17, 2010 in Chilean Application No. 2989-2008 (7 pgs).
Chilean Official Action + Translation dated Jan. 3, 2011 in Chilean Patent Application No. 2989-08 (7 pgs).
Chinese Examination Decision (with translation) issued in application No. 201180005390.6, dated Jul. 28, 2015 (22 pgs).
Chinese Notice of Reexamination (w/translation) issued in application 201180005390.6, dated Feb. 25, 2015 (10 pgs).
Chinese Office Action issued in corresponding Chinese Patent Appln. Serial No. 201180005390.6 dated May 30, 2014, with English text translation (9 pgs).
Chinese Office Action issued in corresponding Chinese Patent Appln. Serial No. 201180005390.6 dated Oct. 18, 2013 (13 pgs).

(56) References Cited

OTHER PUBLICATIONS

Chinese Official Action + Translation dated Apr. 15, 2010 in Chinese Application No. 200810001282.1 (6 pgs).
Chinese Official Action + Translation dated Apr. 17, 2009 in Chinese Application No. 03805787.5 (8 pgs).
Chinese Official Action + Translation dated Dec. 19, 2008 in Chinese Application. No. 200580005999.8, (5 pgs).
Chinese Official Action + Translation dated Jan. 18, 2011 (7 pgs).
Chinese Official Action + Translation dated Oct. 31, 2008 in Chinese Application No. 03805787.5 (9 pgs).
Drug Information Handbook, Lexi-Comp, Inc.: Hudson, OH, pp. 461-462 and 768-769 (4 pgs).
English translation of Examiner's Report dated Feb. 25, 2010, in Japanese Application No. 2003-526459(1 pg).
English translation of Pakistan Examination Report (as reported by foreign agent) in Pakistan Patent Application No. 171/2009 (3 pgs).
EPO Office Action dated Feb. 16, 2009 in EPO Patent Application No. 02761817.2 (6 pgs).
Examination Report dated Aug. 30, 2010 in New Zealand Application No. 572520 (2 pgs).
Examination Report issued by Intellectual Property Office of New Zealand for Appln. Serial No. 549589, dated Feb. 25, 2009 (2 pgs).
Extended European Search Report issued in application No. 11732098.6, dated Mar. 3, 2015 (6 pgs).
International Preliminary Report on Patentability issued for corresponding PCT/US2011/020252, dated Jan. 5, 2010 (10 pgs).
International Search Report and Written Opinion dated Aug. 17, 2010 in PCT/US10/40822 (8 pgs).
International Search Report and Written Opinion dated Aug. 20, 2010 in PCT/US10/40815 (12 pgs).
International Search Report and Written Opinion dated Jul. 13, 2009 in PCT/US09/35305 (7 pgs).
International Search Report and Written Opinion dated Jul. 21, 2010 in PCT/US10/035817 (9 pgs).
International Search Report and Written Opinion dated Mar. 8, 2011, in PCT/US11/20252 (12 pgs).
Japanese Office Action (w/translation) issued in related application No. 2012-548100, dated Jul. 4, 2014 (6 pgs).
Japanese Office Action issued in application No. 2012-548100, dated Feb. 5, 2016 (7 pgs).
Japanese Office Action issued in application No. 2014-210159, dated Sep. 25, 2015 (5 pgs).
Manual of Medical Therapeutics, Woodley et al., 27th Edition, Department of Medicine, Washington University, 1992, pp. 366-367 (4 pgs).
Notice of Allowance issued in U.S. Appl. No. 12/985,158, dated Feb. 12, 2015 (26 pgs).
Office Action issued in U.S. Appl. No. 12/985,158, dated Aug. 30, 2013 (15 pgs).
Office Action issued in U.S. Appl. No. 12/985,158, dated Feb. 20, 2013 (40 pgs).
Office Action issued in U.S. Appl. No. 12/985,158, dated Jul. 21, 2014 (30 pgs).
Office Action issued in U.S. Appl. No. 14/056,828, dated May 3, 2016 (119 pgs).
Office Action issued in related U.S. Appl. No. 12/985,158, dated Nov. 20, 2014 (24 pgs).
Official Action + Translation dated Feb. 19, 2009 in Japanese Patent Application No. 2003-575879 (3 pgs).
Official Action dated Dec. 14, 2009 in U.S. Appl. No. 11/425,097 (6 pgs).
Official Action issued for U.S. Appl. No. 11/680,084, dated Mar. 16, 2010 (14 pgs).
Philippine Office Action issued in related application No. 1/2012/501114, dated Oct. 30, 2014 (3 pgs).
Philippines Office Action issued in application No. 1/2014/501462, dated Apr. 19, 2016 (2 pgs).
Philippines Substantive Examination Report issued in related application No. 1/2012/501114, dated Jun. 5, 2012 (2 pgs).
Physician's Desk Reference (PDR-Online), www.thomsonhc.com, accessed Nov. 18, 2006 (3 pgs).
Science News, vol. 151, p. 205, "Ink Jets not just for the Printed Page", Apr. 5, 1997.
Search Report and Written Opinion dated Nov. 30, 2009 in Singapore Application No. 200807473-4 (16 pgs).
Search Report and Written Opinion issued by Intellectual Property Office of Singapore for Appln. Serial No. 200604852-4, dated Jan. 19, 2009 (8 pgs).
Search Report dated Dec. 2, 2009 in EPO Patent Application No. 07781365.7 (10 pgs).
Search Report dated Jul. 15, 2010 in Singapore Application No. 2009055799 (8 pgs).
South Korean Notice of Preliminary Rejection + Translation dated Feb. 11, 2009 in South Korean Patent Application No. 10-2004-7003223 (7 pgs).
South Korean Notice of Preliminary Rejection + Translation dated Aug. 26, 2009 in South Korean Patent Application No. 10-2004-7003223 (5 pgs).
Substantive Examination issued in corresponding Malaysian Patent Appln. No. PI 2012003067, dated Jan. 29, 2016 (4 pgs).
Sucker et al., "Feste orale und perorale Arzneiformen", Pharmazeutische Technologie, No. 2, 1991, p. 326, XP00214673.
Taiwan Office Action issued in application No. 100100398, dated Mar. 8, 2016 (15 pgs).
Chinese Office Action (w/translation) issued in application No. 201510711869.1, dated Feb. 2, 2019 (9 pgs).
Chinese Office Action (w/translation) issued in application No. 201510711869.1, dated Apr. 2, 2018 (9 pgs).
Chinese Office Action (w/translation) issued in application No. 201510711869.1, dated Aug. 20, 2018 (9 pgs).
Japanese Office Action issued in application No. 2016-096893, dated Feb. 28, 2017 (7 pgs).
U.S. Appl. No. 12/985,158, filed Jan. 5, 2011.
U.S. Appl. No. 14/056,828, filed Oct. 17, 2013.

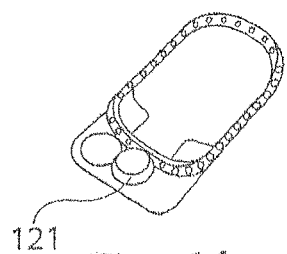
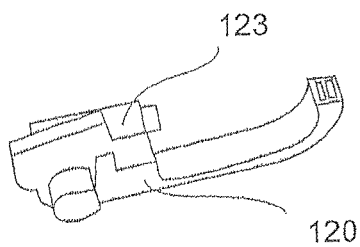
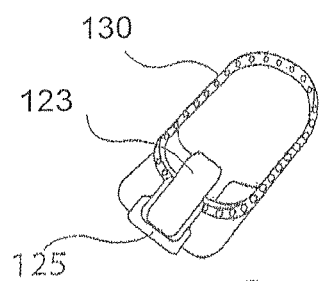
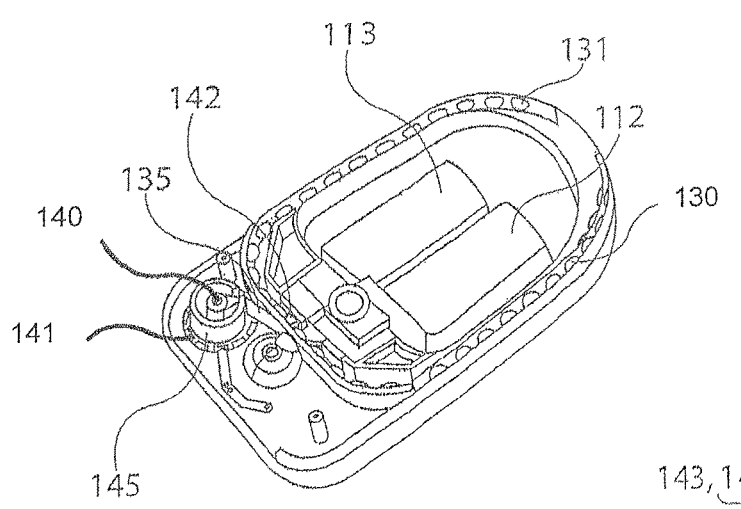
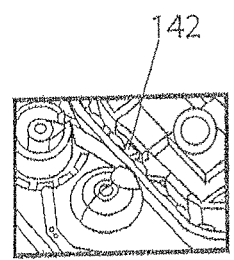
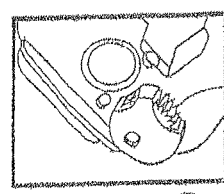
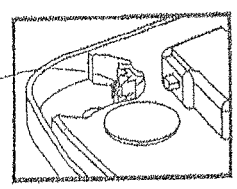

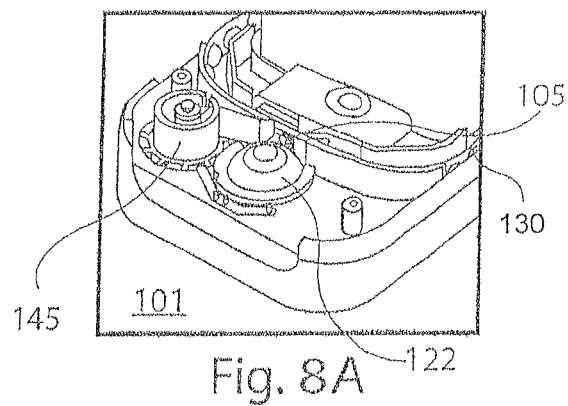
Fig. 8A
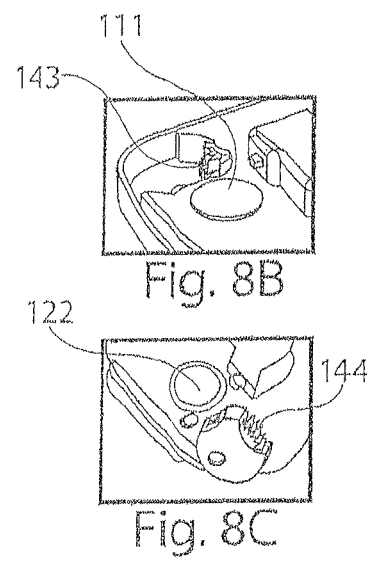
Fig. 8B
Fig. 8C
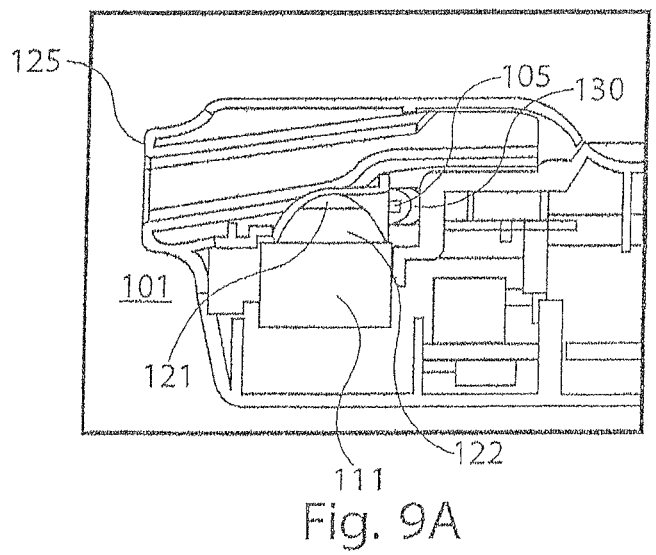
Fig. 9A
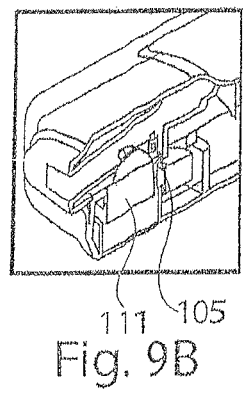
Fig. 9B

INHALATION DEVICE AND METHOD

CROSS REFERENCE TO RELATED APPLICATION

This application is a continuation application of U.S. patent application Ser. No. 14/056,828, filed Oct. 17, 2013, now U.S. Pat. No. 9,974,909, which in turn is a divisional application of U.S. patent application Ser. No. 12/985,158, filed Jan. 5, 2011, now U.S. Pat. No. 8,991,390, which claims priority from the U.S. Provisional Application Ser. No. 61/292,401, filed Jan. 5, 2010; U.S. Provisional Application Ser. No. 61/292,403, filed Jan. 5, 2010; and U.S. Provisional Application Ser. No. 61/292,404, filed Jan. 5, 2010; the contents of which are incorporated herein in their entirety, by reference.

FIELD OF THE INVENTION

The present disclosure relates generally to the field of inhalation devices. The disclosure has particular utility in connection with the delivery of powdered medications to a patient using a dry powder inhaler, and will be described in connection with such utility, although other utilities are contemplated.

BACKGROUND OF THE INVENTION

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles may develop an electrostatic charge on themselves during manufacturing and storage. This may cause the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms. For example, in the case of albuterol, a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will likely be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. Nos. 3,948,264 and 5,458,135.

In prior U.S. Pat. Nos. 7,318,434, 7,334,577 and 7,779,837 incorporated herein by reference, and assigned to the common assignee MicroDose Technologies, Inc., there is provided an improvement over prior art inhalers that utilize vibration to facilitate suspension of power into an inhaled gas stream and which utilizes synthetic jetting to aerosolize drug powder from a blister pack or the like. As taught in the aforesaid U.S. Pat. Nos. 7,318,434, 7,334,577 and 7,779,837 there is provided a dry powder inhaler having a first chamber such as a blister pack or other container, for and holding a dry powder, and a second chamber connected to the first chamber via a passageway for receiving an aerosolized form of the dry powder from the first chamber and for delivering the aerosolized dry powder to a user. A vibrator is coupled to the dry powder in the first chamber. The vibrator is energized and coupled to the first chamber and drives the powder from the chamber by synthetic jetting.

As described in U.S. Pat. No. 7,080,644 also incorporated herein by reference, and also assigned to common assignee MicroDose Technologies, Inc., controlled aliquots or doses of a medication or drug are pre-packaged in a blister pack, which includes a frangible crowned top element which may be conical, conical with a rounded point, rounded, or other raised shape configuration, and a bottom element which may be a flat web or membrane, or which itself may be of shaped configuration, e.g. conical, round, dish shaped, etc. for closely engaging with an underlying vibrating element, the shape and size of which is chosen to provide optimum controlled delivery of a given medication or drug. The top element of the blister pack is pierced with a piercing device such as a sharp needle to form one or more apertures for delivery of the medication or drug contained within the blister pack. The hole pattern and hole size is selected to provide optimization of delivery of the particular medication or drug packaged therein.

SUMMARY OF THE INVENTION

The present disclosure in one aspect provides an improvement over the prior art devices such as discussed above by providing a compact size pharmaceutical delivery package for delivering a pharmaceutical to the airway of a human or animal patient, containing a plurality of individual doses of a pharmaceutical. The delivery package is comprised of a dose drum in the form of a cylinder which includes a plurality of dose compartments for containing the individual doses of a pharmaceutical and a sheath for surrounding the dose drum so as to contain and segregate the plurality of individual doses of a pharmaceutical in the dose compartments. The pharmaceutical delivery package may be formed to fit tightly around an outer surface of the dose drum, wherein the sheath has at least two holes, including a first hole for filling the dose compartment with a pharmaceutical and a second hole for allowing the delivery of one of said plurality of individual doses of a pharmaceutical. Alternatively the sheath may be formed of a tape or foil that may be peeled away or perforated to access the pharmaceutical dose contained therein.

Another aspect of the present invention provides an inhaler for delivering a pharmaceutical to the airway of a human or animal patient. The inhaler comprises a dose drum formed into a cylinder, the dose drum including a plurality of dose compartments for containing individual doses of a pharmaceutical; a sheath surrounding the dose drum; a dose chamber; and a flow channel, through which the individual dose is delivering to the airway of the patient. The dose chamber may be a resonance chamber coupled to a vibration device, such as a piezo-electric device. The inhaler may further include a drive for advancing the dose drum so that individual doses may be loaded into the dose chamber.

Another aspect of the present disclosure provides a method of delivering a pharmaceutical material to the airway of a human or animal patient, the method comprising the steps of providing the pharmaceutical material in a reservoir connected to a metering device; metering the pharmaceutical material with the metering device to form a single pharmaceutical dose; moving the single pharmaceutical dose into a dose chamber; deaggregating the pharmaceutical material of the single pharmaceutical dose; and delivering the single pharmaceutical dose from the dose chamber to the airway of the patient via a flow channel.

Another aspect of the present disclosure provides an inhaler for delivering a pharmaceutical dose to the airway of a human or animal patient. The inhaler includes a reservoir that contains a pharmaceutical material in bulk form, a metering recess for metering the pharmaceutical material to form a pharmaceutical dose; a dose chamber; and a flow channel connected to the dose chamber, through which the pharmaceutical dose is delivered from the dose chamber to the airway of the patient. The metering recess may be located on the outer surface of a metering drum, which is rotated to load the metering recess and load the pharmaceutical dose into the dose chamber, the metering drum being surrounded by a sheath. Alternatively, the metering recess may be enclosed between a first metering door and a second metering door. The reservoir may be in the shape of a cylinder, the reservoir having a compression spring and piston for loading the pharmaceutical into the recess.

Another aspect of the present disclosure provides an inhaler for delivering a pharmaceutical material to the airway of a human or animal patient, the inhaler including a dose chamber with a chamber seal and a flow channel. The dose chamber is sized to contain multiple doses of the pharmaceutical material. The dose chamber may be a resonance chamber that is coupled to a vibration device. The chamber seal may be connected to a pressurized source, such as a nitrogen chamber or a vacuum. The chamber seal may alternatively be connected to a desiccant source.

Yet another aspect of the present disclosure provides a method of delivering a single dose of a pharmaceutical material to the airway of a human or animal patient. Multiple doses of the pharmaceutical material are contained in a resonance chamber. The pharmaceutical material is deaggregated using a vibration device coupled to the resonance chamber, thereby causing a synthetic jet to expel some of the pharmaceutical material. The delivery of the pharmaceutical material is metered by controlling the duration of operation of the vibration device, and may also be controlled by optimizing the vibrating frequency of the vibration device.

Still another aspect of the present disclosure provides a pharmaceutical delivery package in the form of a cartridge, which may be reusable. The cartridge contains a blister strip, formed on a substrate material, with a series of depressions or wells formed therein to contain individual doses of a pharmaceutical. A foil is placed over the substrate to seal the individual depressions, which serve to form individual blisters. The cartridge also includes an aerosol chamber for deaggregating the individual dose of a pharmaceutical and a device for advancing the blister strip relative to the aerosol chamber. The device for advancing the blister strip may comprise one or more of an arm, a spring, a cam, a gear, or a wheel. A blister detection switch facilitates controlling the advancement of the blister strip to consistently position individual blisters relative to the aerosol chamber. The cartridge also includes a device for removing the foil from the blister strip as it is advanced relative to the aerosol chamber. The cartridge also includes a mouthpiece and a flow channel, the flow channel connecting the aerosol chamber and the mouthpiece.

Another aspect of the present disclosure provides an inhaler for delivering a pharmaceutical to the airway of a human or animal patient, utilizing the cartridge described above. The inhaler comprises a housing for a vibrating device and a motor. The cartridge should be formed in a loop, with the blister strip being contained within the loop. The housing include an air inlet and a pressure sensor, the air inlet interfacing or mating with the flow channel of the cartridge. An o-ring or the like may be used to seal the connection between the air inlet and the flow channel. The vibrating device, which may be a piezoelectric device, interfaces with the aerosol chamber of the cartridge. The aerosol chamber may form a resonant chamber. The motor also interfaces with the cartridge, providing the power for driving the device for advancing the blister strip and the device for removing the foil.

Yet another aspect of the present disclosure provides an inhaler for automatically delivering a pharmaceutical to the airway of a human or animal patient. The inhaler comprises a housing containing at least one dose of a pharmaceutical, a pressure sensor, a vibrating device, and an aerosol chamber. The housing is connected to an interface for delivering the pharmaceutical to the patient, and through which the patient breathes.

BRIEF DESCRIPTION OF THE DRAWINGS

Further features and advantages of the present disclosure will be seen from the following detailed description, taken in conjunction with the accompanying drawings, wherein

FIGS. 6A, 6B and 6C, are sectional views of the pharmaceutical delivery package shown in FIG. 4;

FIGS. 7A, 7B, 7C and 7D; 8A, 8B and 8C; 9A and 9B; and 10A, 10B and 10C are sectional views of the pharmaceutical delivery package and device of FIG. 4 assembled together;

DETAILED DESCRIPTION OF PREFERRED EMBODIMENTS

Figures 1A, 1B:
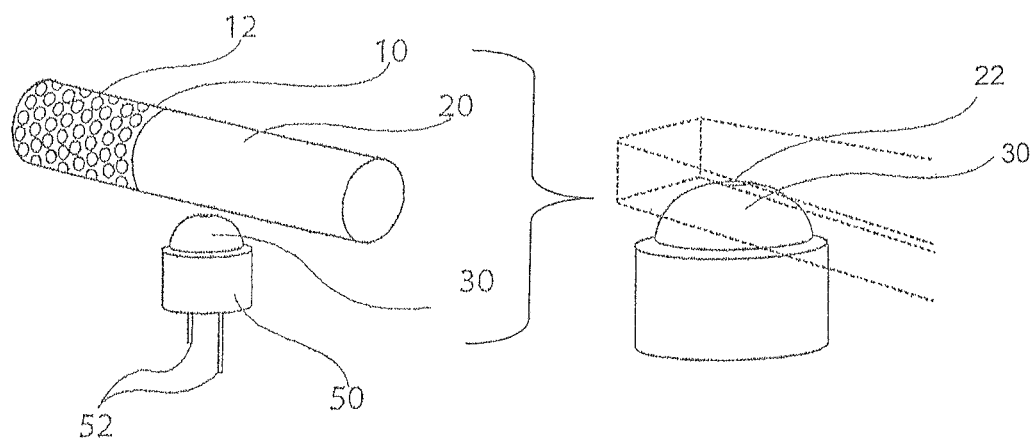
FIGS. 1A-D, are drawings showing a pharmaceutical delivery package and inhaler of the present disclosure.
Figures 1C, 1D:
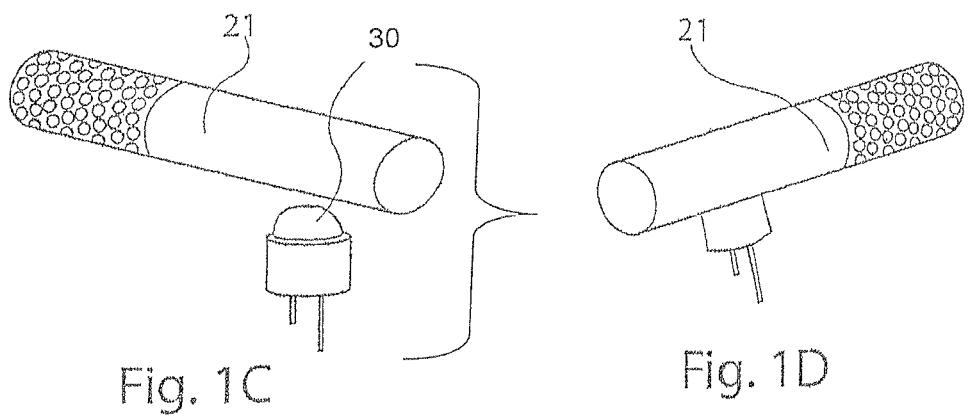

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

The present disclosure provides an improved inhalation device and method for delivering a pharmaceutical to the airway of a patient. The intended patient may be either human or animal and the inhalation device should be designed accordingly. The inhaler will be discussed in connection with a dry powder inhaler, but it is foreseeable that the present disclosure also will be useful in other types of inhalers.

In a first aspect, the present disclosure provides a package for delivering discrete doses of a pharmaceutical, wherein the individual doses are segregated into individual compartments arranged in a pattern on a cylindrical dose drum. The individual doses may be deposited in individual blisters, such as described in commonly-owned U.S. application Ser. No. 11/425,097, incorporated by reference herein. The individual doses may also be encapsulated in between membranes or between a membrane and a substrate, which may or may not be formed with preformed dimples or other indentations to form part of the compartments.

The individual compartments are arranged in a pattern on the cylindrical dose drum, which comprises a substrate formed into a cylindrical shape, the dose drum having an inner face and an outer face. The compartments that contain individual doses of pharmaceuticals may be formed either on the inner face of the substrate or the outer face of the substrate. Alternatively, the compartments may be formed protruding from the substrate at least partially on both the inner surface and outer surface. The substrate may be made from any suitable material, such as for example a plastic, ceramic, paper or metal material, and may range from transparent to opaque in appearance.

In one example of the present aspect of the disclosure, the dose drum is formed of a substrate material configured into a cylinder having an arrangement of dimples, each dimple comprising a recessed volume configured to protrude from the substrate towards the center of the dose drum. The individual dose compartments are formed by the dimples and constrained by a sheath. Referring to FIGS. 1A-D, the sheath 20 may be formed to fit over the dose drum 10 according to a tight tolerance to sufficiently segregate the individual dose compartments 12. In this regard, the sheath may comprise a tightly fitting sleeve that will surround the dose drum for the purposes of containing each dose in its respective dose compartment and provide a moisture barrier for drug preservation or stability. The drum sheath may be configured with a filling access porthole 21 in its surface to allow filling the compartments with the chosen pharmaceutical, and a dose porthole 32 for emptying the dose compartment into dose chamber 30.

Figure 2:
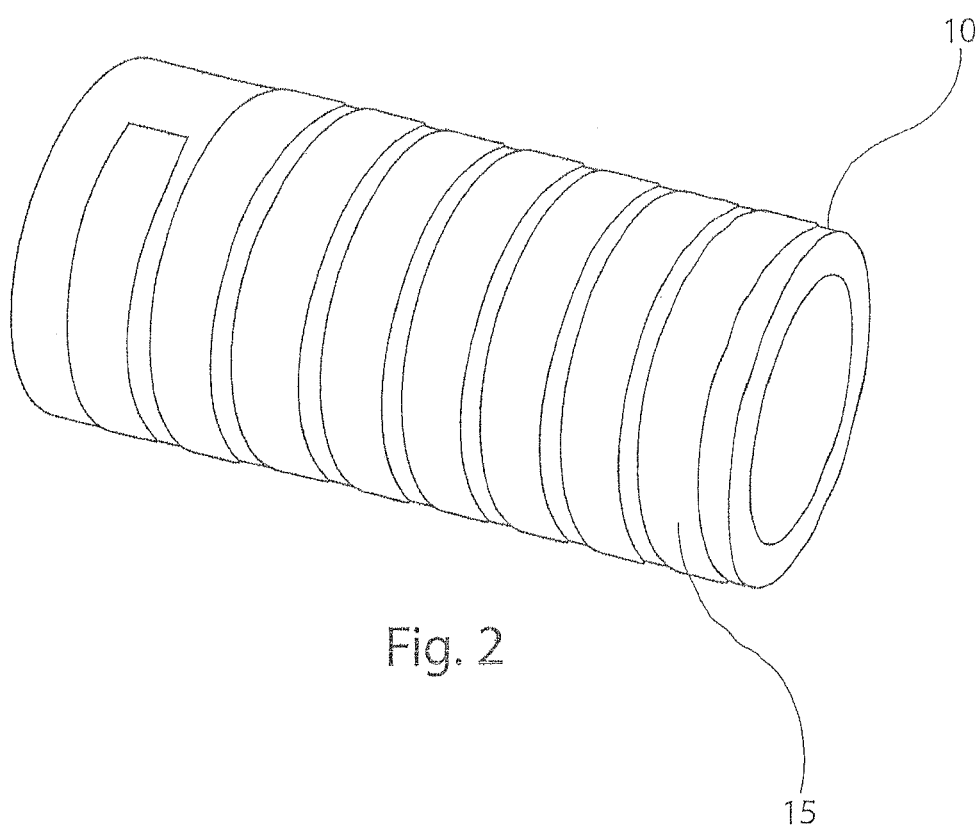
FIG. 2 is a drawing of a dose drum according to one example of the present disclosure.

The sheath also may be formed of a membrane, such as a tape, foil, or film material, which may adhere to the dose drum in order to segregate the individual doses. The membrane should be sufficiently strong to hold the pharmaceutical material, but may also be designed to be perforated or removed, with respect to a single dose compartment, as an individual dose is ready to be loaded into the dose chamber of an inhaler. An example of this alternative design is shown in FIG. 2, wherein the dimples (not visible) are formed in a helical pattern on the dose drum and the sheath comprises a strip of peelable film, foil or tape 15.

Figure 3A:
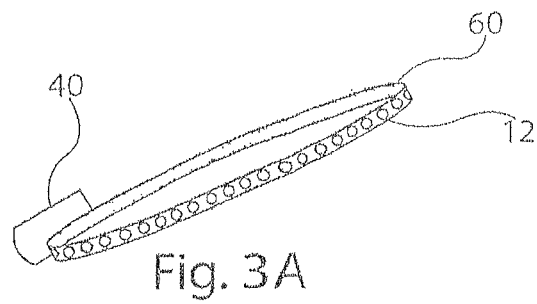
FIGS. 3A-C are drawings of a pharmaceutical delivery package and inhaler in an alternative example of the present disclosure.
Figure 3B:
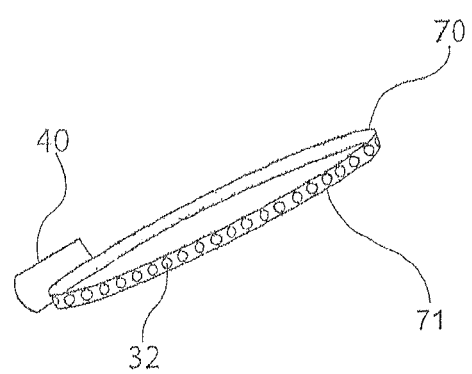
Figure 3C:
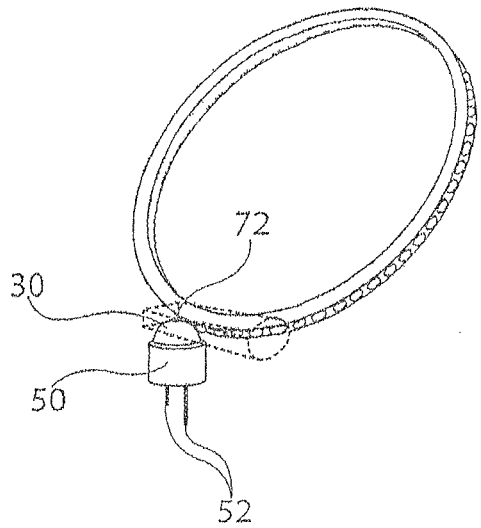
Figure 4:
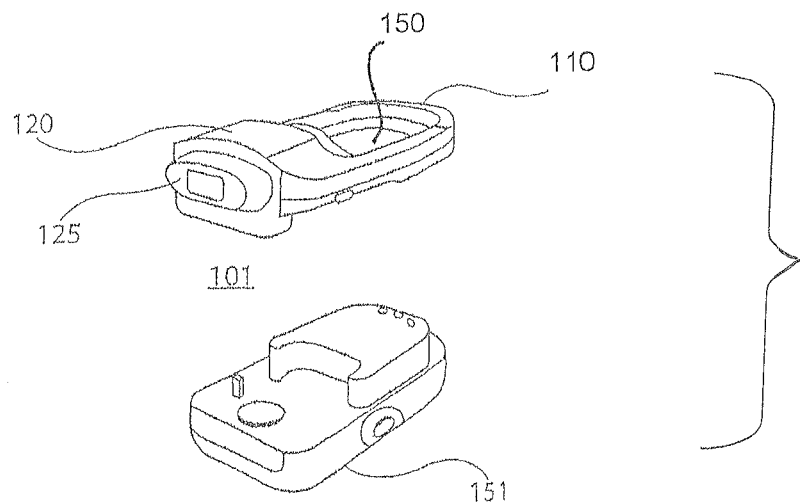
FIG. 4 is a drawing of a pharmaceutical delivery package and delivery device according to another example of the present disclosure.
Figure 5:
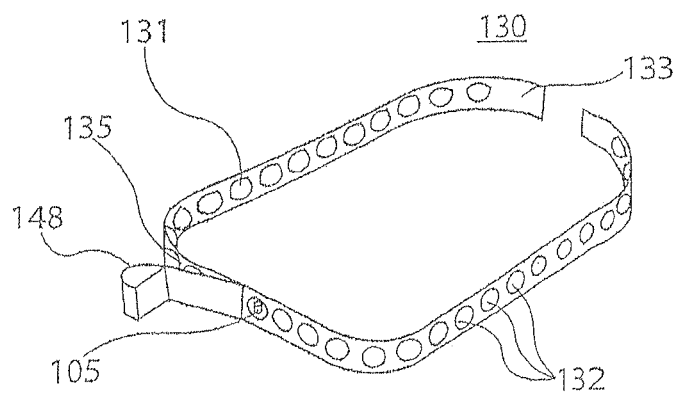
FIG. 5 is a drawing of a blister strip in accordance with the example shown in FIG. 4.
Figure 10A:
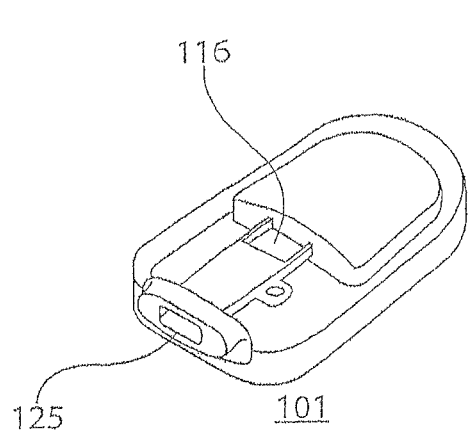
Figure 10B:
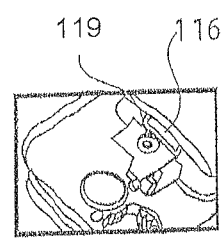
Figure 10C:
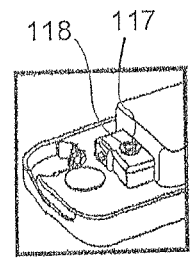
Figure 11A:
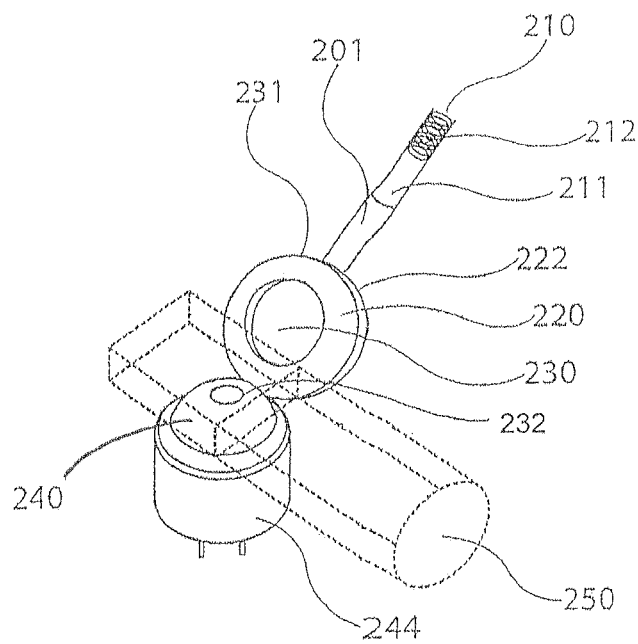
FIGS. 11A and 11B are drawings showing different views of an inhalation device in accordance with the present disclosure.
Figure 11B:
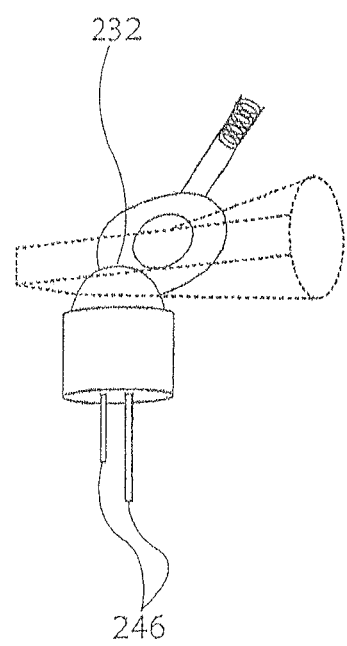
Figure 12A:
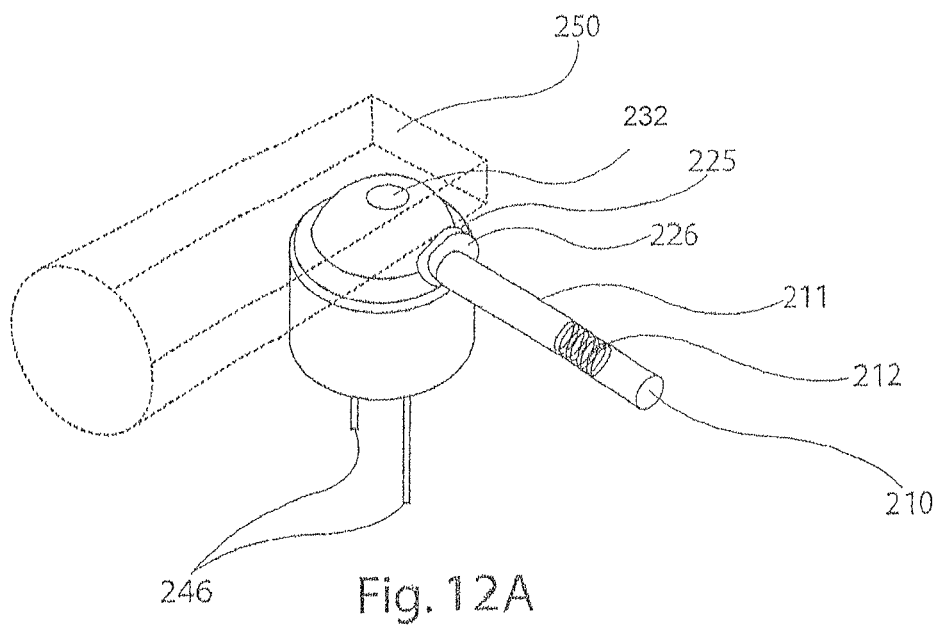
FIGS. 12A and 12B are drawings showing different views of another inhalation device in accordance with the present disclosure.
Figure 12B:
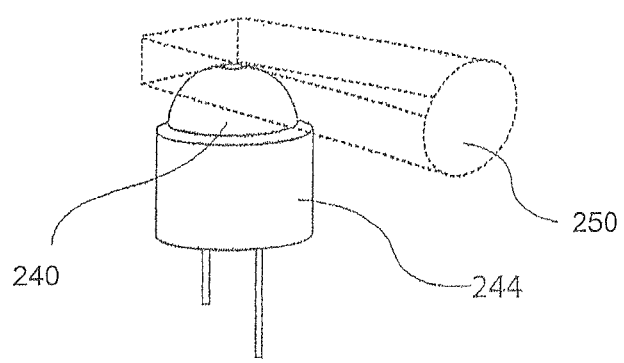

FIGS. 3A-C demonstrate another example of the present disclosure. In this example, the cylinder forming the dose drum is increased in diameter and reduced in height, forming a dose ring 60. The dose ring takes the form of a circular band with compartments arranged circumferentially that will accept pre-metered drug weights and/or volumes. The dose ring may be connected to a drive that will cause the ring to advance in a rotary direction. Whereas the dose drum of FIGS. 1A-D has a height that is greater than one row of dose compartments, the dose ring is only the height of a single row of dose compartments.

The sheath of the present disclosure is adapted in the present example to form ring sheath 70, a tightly fitting sleeve that surrounds the dose ring for the purposes of containing each dose in its respective dose container and providing a moisture barrier for preservation of the pharmaceutical substance. Similar to the sheath above, the ring sheath will have a filling access porthole 71 and a dose porthole 72, the latter of which is connected to the dose chamber. Similar to the dose drum above, the ring sheath could be replaced with a peelable film, foil or tape that would be removed from each dose container just prior to being exposed to the dosing chamber.

The dose drum of the present disclosure may be loaded with individual doses by being mated with a hopper containing a desired pharmaceutical, wherein the geometry of the individual dose compartments may serve to help meter the pharmaceutical.

The dose drum may be manufactured as a reusable component of an inhaler or as a disposable pharmaceutical dose container. The particular design may instruct as to what materials are suitable for use in the construction of the dose drum.

Another aspect of the present disclosure provides an inhaler for delivering a pharmaceutical to the airway of a human or animal patient utilizing a dose drum as described above. Referring again to FIGS. 1A-D, the inhaler comprises a dose drum 10, having a cylindrical substrate with a plurality of dose compartments 12 disposed thereon, a dose chamber 30 for accepting the individual pharmaceutical dose from individual dose compartments prior to delivery to the patient, and a flow channel 40 adjacent to the dose chamber for carrying the pharmaceutical to the airway of the patient.

The dose chamber 30 may comprise a resonance chamber, having a volume and shape that will acoustically resonate at a chosen frequency. The resonance chamber may in turn be coupled to a vibration device 50, such as a piezoelectric transducer, to provide vibratory energy for utilizing the acoustic properties of the resonance chamber to create a synthetic jet, as described in commonly-owned U.S. Pat. Nos. 7,318,434, 7,334,577 and 7,779,837, the contents of which patents are incorporated herein by reference. The resonance chamber will receive an individual dose from the dose drum via dose porthole 22. Other examples of appropriate vibrating devices are disclosed in commonly-owned U.S. patent application Ser. No. 11/060,267, incorporated herein by reference.

The pharmaceutical material is then de-agglomerated and expelled into the flow channel 40 by synthetic jetting through dosing holes 32. The dosing holes promote the formation of a synthetic jet and facilitate the transfer of the pharmaceutical from the dosing chamber into the flow channel. The size of the holes can effect synthetic jet velocity and, ultimately, fine particle distribution.

The vibration device 50 is connected to a power supply 52. The vibration device may further be connected to a frequency generator for optimal performance, such as is described in commonly-owned co-pending U.S. application Ser. No. 12/392,686, incorporated herein by reference.

The inhaler may utilize a placement device for advancing the dose drum and aligning a particular dose compartment with the dose porthole of the sheath. The placement device may be, for example, a screw-drive device. The placement device may influence the chosen geometric arrangement of the dose compartments about the surface of the dose drum, such as shown in FIG. 2, for example.

The inhaler of the present disclosure may further comprise a chamber seal. The chamber seal may be in the form of a stopper that prevents the passage of air into the dose chamber when the device is idle. This is included to further avoid unwanted exposure of individual doses to moisture, oxygen and other contaminants. The chamber seal will open on authorization signal from the inhaler, such when the inhaler senses the patient inhaling (see, for example, U.S. Pat. No. 6,152,130 and U.S. Published Application Serial No. 2005/0183725, both assigned to the common assignee), and close after the dose is complete.

The chamber seal may further be connected to a pressurized nitrogen chamber by a nitrogen line that would fill the dose chamber with nitrogen between doses. It could also be connected to a vacuum source to evacuate air and moisture between doses. This may be done using at least a portion of the same nitrogen line. The chamber seal may also be connected to a desiccant chamber to absorb moisture transferred from the atmosphere during dosing.

The device of the present disclosure is susceptible to modification. For example, the dose chamber may be connected to multiple dose drums for delivering combination pharmaceutical products.

Referring to FIGS. 4-11, another aspect of the present disclosure provides an inhaler 101 utilizing a pharmaceutical delivery package in the form of a cartridge 120, which cartridge may be reusable or disposable. The principle of operation for this device is in similar to the above-described device, and as further described in the afore-mentioned commonly-owned patents. In particular, U.S. Patent Publication No. 2010/0294278, incorporated by reference herein, describes a compact inhaler wherein the plurality of individual doses of a pharmaceutical are contained in a rotary cassette. The cassette contains a radial arrangement of individual blisters. The inhaler described therein is similar in many ways to the present aspect of the disclosure, except in that the rotary cassette is replaced by a cartridge 120 containing a blister strip 130. Other differences may be apparent from the discussion that follows.

As seen in FIGS. 4-10, the inhaler generally comprises a housing 110 and a cartridge 120. As with previous disclosures, the inhaler includes a mouthpiece 125 and a vibrating device 111. The mouthpiece is connected to a flow channel 123, which is connected to an aerosol chamber 121, situated adjacent to the vibrating device. Unlike previous examples, however, the mouthpiece, flow channel and aerosol chamber are incorporated into the cartridge 120. This arrangement affords advantages in reducing the size of the inhaler, drug protection and maintaining performance.

The cartridge 120 contains a blister strip 130, which is comprised of a substrate 133, such as a cold-formed plastic, with a series of depressions 132 or wells formed therein to contain the individual doses 105. A foil, film or tape 135 is placed over the substrate to seal the individual depressions, which form individual blisters 131 filled with the pharmaceutical. The cartridge also includes an aerosol chamber 121, in which the individual doses are deaggregated according the methods described above and in the above-referenced applications. The aerosol chamber is preferably a resonance chamber, as described herein, and is bounded by a membrane 122 which contacts the vibrating device 111 when assembled.

In the example shown, the cartridge also includes an advancing device 140 for advancing the blister strip 130 relative to the aerosol chamber 121. The device for advancing the blister strip may comprise an arm, a spring, a cam, a gear, a wheel, or any combination thereof. For example, FIG. 5 shows a pilot loop 148, which engages the blister strip, similar to a combination of a spring and an arm, in order to advance the blister strip. A blister detection switch 142 senses the advancement of the blister strip and facilitates controlling the advancement of the blister strip to consistently position individual blisters relative to the aerosol chamber 121.

The cartridge also includes a foil, film or tape removal device 141 for removing the foil, film or tape from the blister strip as it is advanced relative to the aerosol chamber. The foil, film or tape removal device includes a take-up spool 145. Once the foil, film or tape is removed, the individual dose 105 is emptied into the aerosol chamber 121 for delivery to the patient.

The arrangement of the blisters 131 on blister strip 130 facilitates, or necessitates, the formation of the cartridge 120 in a loop, i.e., having an open area 150 in the center. The housing includes a complementary protrusion 151. Within the protrusion, the housing contains a battery 112 and motor 113. The motor turns gears 143,144, and thereby drives the take-up spool 145 and foil removal device 141. The battery also provides power to the vibrating device 111, which may be a piezoelectric device. The battery also may be carried on the cartridge, and replaceable with the cartridge. Alternatively, the blister strip may be advanced by a thumb-screw, lever or clock mechanism, for example.

In the example shown, the housing further includes an air inlet 116, which connects to the flow channel 123 of the cartridge. An o-ring 119 may be placed to facilitate a seal at the interface between the flow channel and the air inlet. A pressure sensor 117, powered by the battery, is located in a pressure sensor port 118 near the air inlet in order to sense the breathing of the patient through the inhaler.

The present aspect is subject to modification in accordance with the other examples contained herein and in the commonly-owned patents incorporated by reference. For example, the inhaler could be constructed with the mouthpiece 125, flow channel 123, aerosol chamber 121, or any combination thereof, forming part of the main housing 110 instead of the cartridge 120.

The present disclosure further provides a method and device for metering a pharmaceutical material into a dosage amount and delivering that dose to the airway of a patient.

For example, one aspect of the present disclosure provides an inhaler for delivering a pharmaceutical dose to the airway of a patient. The intended patient may be either human or animal and the inhalation device should be designed accordingly. The inhaler will be discussed in connection with a dry powder inhaler, but it is foreseeable that the present disclosure will also be useful in modifying the designs of other types of inhalers.

The inhaler includes a reservoir, which contains a pharmaceutical material in bulk form. Referring to FIGS. 11A-B and FIGS. 12A-B, one advantageous shape of the reservoir may be a cylinder wherein the reservoir includes a piston 211 and compression spring 212 to assist in emptying the reservoir. Other shapes, such as spheres, cones and so forth, are also available and the figures are not meant to limit the present disclosure to the use of a cylindrical reservoir. Other forms of back pressure may be used as an alternative to the piston and compression spring. Similarly, many types of springs, aside from the helical spring shown, are suitable for use with the inhalation device of the present disclosure. A significant advantage of the present disclosure is that the reservoir may be reloaded with bulk material and the device may be reused.

The inhalation device of the present example also includes a metering device for measuring the bulk pharmaceutical material into a single pharmaceutical dose. The metering device should have a metering recess for receiving the pharmaceutical material from the reservoir, the metering recess being sized to receive the desired dose.

Referring to FIGS. 11A and 11B, the metering device may be comprised of a metering drum 220 and a sheath 230. In this example, the metering recess is formed as a metering dimple 222 on the outer surface of the metering drum. The dimple may be formed integral to the metering drum and should be manufactured to a precision volume for the purpose of metering the pharmaceutical dose.

The sheath 230 is formed to fit tightly around the outer surface of the metering drum, but not so tight as to prevent the metering drum from rotating on its axis. The inhalation device may include a drive for rotating the metering drum. The rotation of the metering drum will align the metering recess 222 with one of at least two holes 231,232 in the sheath. The filling access porthole 231 is located on the sheath 230 at the interface with the reservoir 210 and allows the metering recess 222 to be filled with the pharmaceutical material 201. The dose porthole 232, allows the metered pharmaceutical dose to be delivered to a dose chamber 240.

The dose chamber is configured to accept a single pharmaceutical dose, deaggregate the pharmaceutical material, and deliver the material to the flow channel 250. The dose chamber will be configured based upon the various methods that may be used for delivering medication to the patient.

As with the previous examples, the dose chamber may comprise a resonance chamber, having a volume and shape that will acoustically resonate at a chosen frequency. The advantages of this feature are discussed above. Further, as described above, the resonance chamber may be coupled to a vibration device 244, such as a piezoelectric transducer, to provide vibratory energy for utilizing the acoustic properties of the resonance chamber. The vibration device is connected to a power supply 246.

Referring to FIGS. 12A and 12B, the metering device of the present disclosure may comprise a metering recess or metering compartment that is enclosed by at least two metering doors 225, 226. The first metering door 225 sits between the metering compartment and the dose chamber 240. The second metering door 226 is between the metering compartment and the reservoir 210. Thus, when the second metering door opens (the first metering door remaining closed), the metering compartment may be loaded with the pharmaceutical material 201. Then, when the first metering door is opened (the second metering door remaining closed), the metered dose of pharmaceutical material may be placed in the dose chamber.

The present disclosure also provides a method for delivering a pharmaceutical material to the airway of a patient, which may be human or animal, by providing the pharmaceutical material in a reservoir connected to a metering device; metering the pharmaceutical material with the metering device to form a single pharmaceutical dose; moving the single pharmaceutical dose into a dose chamber; deaggregating the pharmaceutical material in the single pharmaceutical dose; and delivering the single pharmaceutical dose from the dose chamber to the airway of the patient via a flow channel.

The method of the present disclosure may be used with a metering device such as described herein comprising a metering drum and a sheath. Alternatively, the metering device may comprise a metering compartment enclosed between a first metering door and a second metering door, wherein the second metering door is opened during the step of metering the pharmaceutical material, and the first metering door is opened during the step of moving the single pharmaceutical dose into the dose chamber.

The dose chamber may serve as a resonance chamber, being coupled to a vibration device, wherein the step of deaggregating the pharmaceutical material involves activating the vibration device to create a synthetic jet thereby delivering the single pharmaceutical dose from the dose chamber to the airway of the patient via a flow channel.

Another aspect of the present disclosure provides a device for metering a pharmaceutical material into a selected dosage amount and delivering that dose to the airway of a patient. The device of the present disclosure is an inhaler that includes a chamber, which contains the pharmaceutical material, and a flow channel for delivering the pharmaceutical material to the patient. Basic functions of each of these elements are described in the commonly-owned disclosures mentioned above.

According to the present disclosure, multiple doses of a pharmaceutical material are stored within a combined reservoir and dosing chamber, which chamber is designed to store multiple doses of the pharmaceutical material, and meter out the pharmaceutical material in predetermined doses.

Figures 13A, 13B:
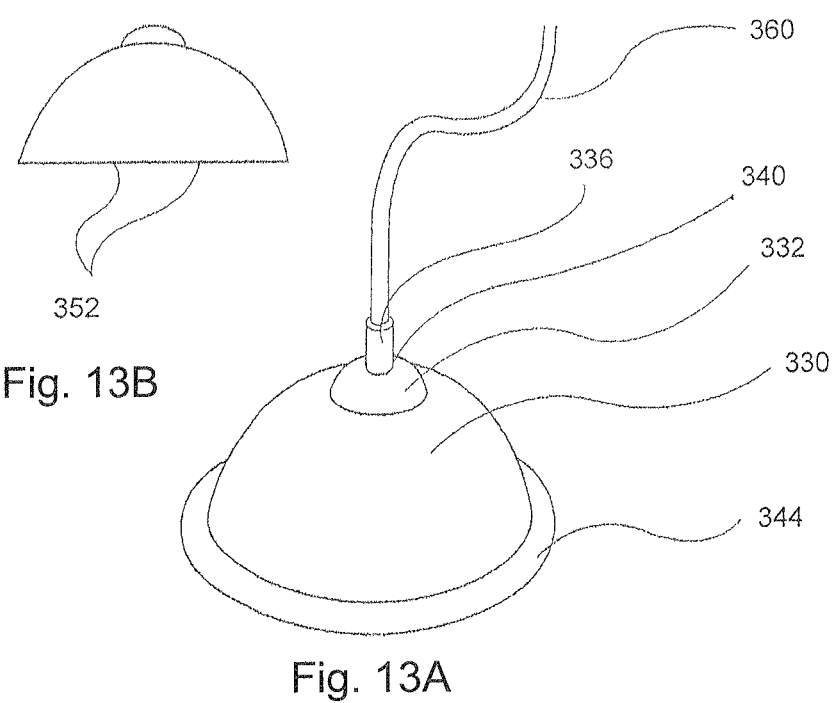
FIGS. 13A and 13B are drawings of a pharmaceutical material delivery package and inhaler in accordance with another example of the present disclosure.

Referring to FIGS. 13A and 13B, an inhaler is illustrated comprising a combined reservoir and dosing chamber which is configured to accept a supply of a pharmaceutical material, deaggregate the pharmaceutical material, and deliver the material to the flow channel 340. The combination reservoir and dosing chamber 330 comprises a resonance chamber, having a volume and shape that will acoustically resonate at a chosen frequency. The resonance chamber and the advantages thereof are discussed in detail above.

The inhaler of the present disclosure optionally may comprise a chamber seal 336. The chamber seal may be in the form of a stopper that prevents the passage of air into the combined reservoir and dosing chamber when the device is idle. This is included to further avoid unwanted exposure of the pharmaceutical material to moisture, oxygen and other contaminants. The chamber seal will open on authorization signal from the inhaler, such as when the inhaler senses the patient inhaling (see previously referenced commonly-owned patents and applications), and close after the dose has been delivered.

The chamber seal 336 optionally may further be connected to a pressurized nitrogen chamber by a nitrogen line 360 that would fill the combined reservoir and dose chamber with nitrogen between doses. Chamber seal 336 also could be connected to a vacuum source to evacuate air and moisture between doses. This may be done using at least a portion of the same nitrogen line 360. The chamber seal also may be connected to a desiccant chamber to absorb moisture transferred from the atmosphere during dosing.

The present disclosure allows the combined reservoir and dosing chamber to hold multiple doses to be expelled by synthetic jetting through dosing hole 332, as described above. The dose size will be controlled electronically by controlling the frequency and duration of each activation. Because the acoustic resonance will be affected by the remaining drug load, each dose activation preferably is electronically tailored to provide consistent drug expulsion for every dose, e.g. by sensing movement of the vibration device and power source, and feedback controlling the power delivered to the vibration device following the teachings of commonly-owned U.S. patent application Ser. No. 12/246,208, incorporated herein by reference.

An example of the present disclosure was tested using a blister that was set up to serve as a resonance chamber for expelling multiple doses. A 4 mg blister was loaded into the test device and the parameters were set to allow from approximately 1 mg of pharmaceutical to be expelled with each dose. This was repeated for additional doses. Blisters were removed and weighed between actuations. In tables 1 and 2, below, it is shown that by varying the "on-time", or the duration of activating the vibration device, doses can be delivered with adequate predictability, even without optimization of the vibrating frequency and pattern.

TABLE 1

| 150 ms on-time | | |
|---|---|---|
| | $1^{st}$ dose | $2^{nd}$ dose |
| 1 | 1.058 | 1.262 |
| 2 | 1.239 | 1.259 |
| 3 | 1.229 | 1.369 |
| Mean | 1.18 | 1.30 |
| SD | 0.10 | 0.03 |
| % RSD | 8.66 | 4.83 |
| Max-Min | 0.18 | 0.11 |

TABLE 2

| 125 ms on-time | | | |
|---|---|---|---|
| | $1^{st}$ dose | $2^{nd}$ dose | $3^{rd}$ dose |
| 1 | 0.991 | 1.054 | 0.932 |
| 2 | 1.09 | 1.052 | 0.808 |
| 3 | 0.931 | 1.108 | 0.914 |
| Mean | 1.00 | 1.07 | 0.88 |
| SD | 0.08 | 0.03 | 0.07 |
| % RSD | 8.00 | 2.97 | 7.57 |
| Max-Min | 0.16 | 0.06 | 0.12 |

The device of the present disclosure is susceptible to modification. Two or more combined reservoir and dosing chambers may be incorporated in a single inhaler for delivering combination pharmaceutical products.

Another aspect of the present disclosure provides a method for delivering a pharmaceutical material to the airway of a patient, which may be human or animal. The method provides a pharmaceutical material contained in a combined reservoir and dosing chamber which also serves as a resonance chamber. The pharmaceutical material is then vibration deaggregated within the combined reservoir and dosing chamber, allowing a single dose to be delivered to the patient via synthetic jetting. The step of deaggregating the pharmaceutical material, thereby creating the synthetic jet, may be performed by controlling the duration in which power is supplied to a vibration device 344 by a power source 352, as described above. The power source also may be a source of frequency control, for further controlling the effectiveness of the synthetic jetting.

The combined reservoir and dosing chamber also serves as a resonance chamber, by being coupled to a vibration device, wherein the step of deaggregating the pharmaceutical material involves activating the vibration device to create a synthetic jet thereby delivering the pharmaceutical from the combined reservoir and dosing chamber to the airway of the patient via a flow channel.

The present disclosure provides unique, space-saving designs which allow for the creation of a smaller delivery devices, conserve materials, enable the pharmaceutical packaging to include an increased number of metered doses in a single package and provides for a mechanism to allow delivery of a dry powder inhalation to patients not currently served by commercial dry powder inhalers.

As used herein the term "pharmaceuticals" is intended to include all forms of drugs suitable for deliver by an inhaler. For example, while the present disclosure is particularly useful with dry powder inhalers (DPIs), the technology may be used to enhance other embodiments of inhalers as well. Therefore, the pharmaceutical referred to in the present disclosure necessarily includes liquid forms of medications as well as dry powdered medications.

Moreover, the term pharmaceuticals should not be strictly construed to exclude other useful substances such as phyto-pharmaceuticals, vitamins, hormones, steroids and other bioactive small molecules, peptides, proteins, etc.

It should be emphasized that the above-described embodiments of the present device, particularly, and "preferred" embodiments, are merely possible examples of implementations and merely set forth for a clear understanding of the principles of the disclosure. Many different embodiments of a pharmaceutical package for an inhaler described herein may be designed and/or fabricated without departing from the spirit and scope of the disclosure. All these and other such modifications and variations are intended to be included herein within the scope of this disclosure and protected by the following claims. Therefore the scope of the disclosure is not intended to be limited except as indicated in the appended claims.

The invention claimed is:

1. An inhaler for delivering a pharmaceutical to the airway of a human or animal patient, comprising:
    a housing containing a vibrating device and a motor or mechanical advancing mechanism;
    a removable cartridge formed to interface with the housing, the cartridge forming a loop surrounding an opening formed completely through a center portion of the cartridge, wherein the removable cartridge further comprises:
        a strip arranged within the loop of the cartridge having a plurality of blisters containing individual doses of a pharmaceutical;
        a flow channel;
        an air inlet that interfaces with the flow channel;
        an aerosol chamber connected to the flow channel, wherein the aerosol chamber and the vibrating device form a resonance chamber for deaggregating the pharmaceutical;
        a mouthpiece connected to the flow channel for delivering the pharmaceutical to the patient;
        a device for advancing the strip relative to the aerosol chamber; and
        a device for opening an individual blister adjacent the aerosol chamber whereupon an individual dose of the pharmaceutical is delivered to the aerosol chamber;
    wherein the vibrating device interfaces with the aerosol chamber.

2. The inhaler of claim 1, wherein the housing further includes a pressure sensor located in or near the air inlet.

3. The inhaler of claim 1, wherein the device for advancing the strip is driven by the motor or at least one mechanical advancing mechanism contained within the housing.

4. The inhaler of claim 1, wherein the vibrating device is a piezoelectric device.

5. The inhaler of claim 1, wherein the pharmaceutical is in a powder form.

* * * * *